(12) United States Patent
Lee

(10) Patent No.: US 12,303,363 B2
(45) Date of Patent: May 20, 2025

(54) SEMIPERMANENT MENSTRUAL PAD

(71) Applicant: Eun Ju Lee, Yangsan-si (KR)

(72) Inventor: Eun Ju Lee, Yangsan-si (KR)

( * ) Notice: Subject to any disclaimer, the term of this patent is extended or adjusted under 35 U.S.C. 154(b) by 478 days.

(21) Appl. No.: 17/955,429

(22) Filed: Sep. 28, 2022

(65) Prior Publication Data

US 2023/0018845 A1    Jan. 19, 2023

Related U.S. Application Data

(63) Continuation of application No. PCT/KR2021/012197, filed on Sep. 8, 2021.

(30) Foreign Application Priority Data

Sep. 29, 2020  (KR) ........................ 10-2020-0126914

(51) Int. Cl.
*A61F 13/475*   (2006.01)
*A61F 5/455*    (2006.01)
*A61F 13/472*   (2006.01)
*A61F 13/505*   (2006.01)

(52) U.S. Cl.
CPC .......... *A61F 13/4753* (2013.01); *A61F 5/455* (2013.01); *A61F 13/505* (2013.01); *A61F 2013/47281* (2013.01)

(58) Field of Classification Search
CPC .......... A61F 5/455; A61F 5/44; A61F 5/4405; A61F 5/4553; A61F 13/4753; A61F 13/505; A61F 13/15268; A61F 13/47227; A61F 13/45; A61F 13/47
See application file for complete search history.

(56) References Cited

U.S. PATENT DOCUMENTS

| 4,270,539 | A | 6/1981 | Frosch et al. |
| 6,428,521 | B1 | 8/2002 | Droll |
| 6,652,503 | B1 * | 11/2003 | Bradley ............... A61F 13/5616 604/385.01 |
| 7,179,247 | B2 | 2/2007 | Mizutani et al. |
| 2005/0027277 | A1 * | 2/2005 | Mizutani ........... A61F 13/47209 604/385.101 |

FOREIGN PATENT DOCUMENTS

| CN | 1694666 A | 11/2005 |
| CN | 204158578 U | 2/2015 |
| EP | 0018749 A1 | 11/1980 |
| KR | 20170006508 A * | 7/2015 |
| KR | 102048943 B1 | 11/2019 |

* cited by examiner

*Primary Examiner* — Jessica Arble
*Assistant Examiner* — Nhu Q. Tran
(74) *Attorney, Agent, or Firm* — Lempia Summerfield Katz LLC

(57) ABSTRACT

A semipermanent menstrual pad may include: a genital area cover configured to cover a female genital area and having a storage space recessed at a center of the genital area cover to store menstrual blood, and a lid part configured to cover an upper portion of the storage space to prevent the menstrual blood introduced into the storage space from leaking to the outside, in which the lid part is coupled to or separated from the genital area cover in an attachable/detachable manner and includes a through-hole through which the menstrual blood is introduced, and a first menstrual blood leak prevention projection formed along a boundary line of the through-hole and provided at a position spaced apart from the through-hole by a preset distance to primarily prevent the leak of the menstrual blood.

11 Claims, 5 Drawing Sheets

SEMIPERMANENT MENSTRUAL PAD

CROSS-REFERENCE TO RELATED APPLICATIONS

This application is a continuation of International Application No. PCT/KR2021/012197, filed on Sep. 8, 2021, which claims benefit of priority to Korean Patent Application No. 10-2020-0126914, filed on Sep. 29, 2020, the entire contents of each of which are incorporated herein by reference.

TECHNICAL FIELD

The present application relates to a semipermanent menstrual pad structure capable of storing and discharging menstrual blood.

BACKGROUND

The statements in this section merely provide background information related to the present disclosure and may not constitute prior art.

In general, women begin to experience menstruation that is the biggest change in body in puberty. Most women use menstrual pads to perform more hygienic and comfortable activities and prevent menstrual blood from leaking to the outside during menstruation.

The menstrual pad has a pad shape and is used by being attached to inner sides of panties by using attachment wings formed at two opposite left and right sides of the menstrual pad. It is very inconvenient for users to wear menstrual pads. If the amount of menstrual blood is large or the user inappropriately wears the menstrual pad, the user's motion often causes a leak of menstrual blood to the outside.

To eliminate the inconvenience caused by the pad-type menstrual pads, tampons, which are menstrual pads used by being inserted into the vagina, have been distributed on the market.

The tampon has a stick-type absorbing material and is structured to be inserted into the vagina to absorb the menstrual blood. The tampon is very advantageous in improving wearability and absorptiveness. However, recently, some users have raised problems that the tampon may cause vomiting or shock syndrome caused by toxicity.

Therefore, silicone menstrual cups, which are harmless to the human body and have excellent resilience, have been distributed on the market. The advantage of the menstrual cup is that the menstrual cup may be easily inserted into the vagina and prevent the menstrual blood from leaking to the outside, thereby maintaining wearing comfort even though the user performs intense activities and motions.

However, we have discovered that although the menstrual cup made of silicone may be reused, the costs required to manufacture the menstrual cup is very high. In addition, because a vacuum is formed inside the vagina during the process of removing the menstrual cup inserted into the vagina, the user cannot easily remove the menstrual cup, causing pain in the user. In particular, if the user forcibly removes the menstrual cup, the menstrual blood is compressed, and thus the menstrual blood contained in the menstrual cup may pour out to the outside. In addition, because post-treatment processes such as a process of treating the menstrual blood and a process of cleaning the treated menstrual cup need to be performed to reuse the menstrual cup, the user may feel uncomfortable. In particular, there are various problems related to the post-treatment process and the processes of carrying and/or storing the menstrual cup while the user is out. The menstrual pad insertable into the body requires very demanding hygiene management. In addition, the menstrual pad insertable into the body needs to be used within the time limit of use to prevent the risk of toxic shock syndrome. In addition, women in young-age groups, such as adolescents, or women who do not have experience in using the menstrual pads, have a great rejection to try to use the menstrual pad insertable into the body.

SUMMARY

An embodiment of the present disclosure provides a semipermanent menstrual pad. The semipermanent menstrual pad includes: a genital area cover configured to cover a female genital area and having a storage space recessed at a center of the genital area cover to store menstrual blood. The semipermanent menstrual pad further includes a lid part configured to cover an upper portion of the storage space to inhibit or prevent the menstrual blood introduced into the storage space from leaking to the outside. In particular, the lid part is coupled to or separated from the genital area cover in an attachable/detachable manner. The lid part includes: a through-hole through which the menstrual blood is introduced; and a first menstrual blood leak prevention projection formed along a boundary line of the through-hole and provided at a position spaced apart from the through-hole by a preset distance to primarily prevent the leak of the menstrual blood. In another embodiment, the genital area cover includes: the storage space configured to store the menstrual blood and covered by the lid part; a protruding portion extending from the storage space and protruding in the upward direction so as to be seated in a space between female buttocks; and a discharge guide groove configured to guide a discharge route for the menstrual blood when the menstrual blood stored in the storage space is discharged to the outside as the lid part is separated from the genital area cover.

According to the embodiment of the present disclosure, because the user does not need to insert the menstrual pad directly into the vagina, the user's burden in wearing and removing the menstrual pad may be reduced. In addition, because the menstrual pad is not inserted into the human body, there is almost no likelihood that the vomiting or the shock syndrome caused by toxicity will occur.

In addition, according to the embodiment of the present disclosure, the menstrual pad is made of medical silicone and has no disposable absorber. Therefore, there are advantages in that the menstrual pad is harmless to the human body, and the menstrual pad is environmental-friendly and economical because the menstrual pad may be semipermanently used by being cleaned and disinfected.

In addition, the embodiment of the present disclosure provides the double menstrual blood leak prevention projection structure for preventing the leak of the menstrual blood. Therefore, there is an advantage in that the menstrual blood does not easily leak even though the user takes various postures and performs various activities.

Further areas of applicability should become apparent from the description provided herein. It should be understood that the description and specific examples are intended for purposes of illustration only and are not intended to limit the scope of the present disclosure.

BRIEF DESCRIPTION OF DRAWINGS

In order that the disclosure may be well understood, there will now be described various forms thereof, given by way of example, reference being made to the accompanying drawings, in which.

Figure 1:
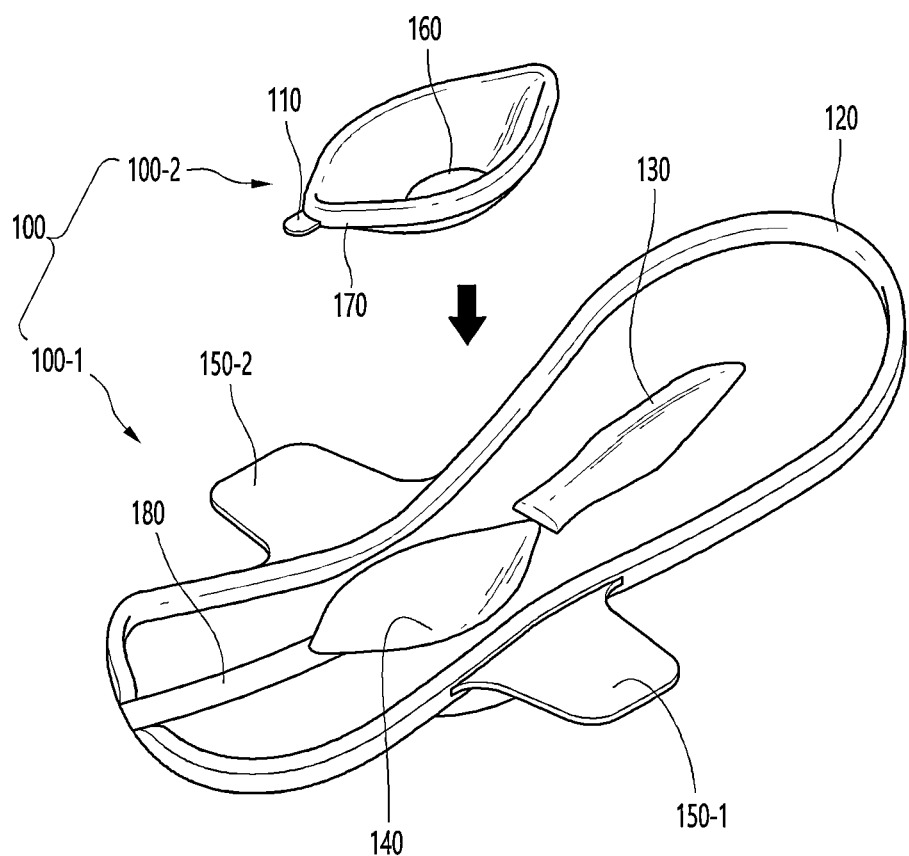
FIG. 1 is an exploded perspective view of a semipermanent menstrual pad according to an embodiment of the present disclosure.

The drawings described herein are for illustration purposes only and are not intended to limit the scope of the present disclosure in any way.

DETAILED DESCRIPTION

The technology described below may be modified in various ways and may have various embodiments, and particular embodiments as illustrated in the drawings are described in detail below. However, the description of the embodiments is not intended to limit the technology described below to the particular embodiments, but it should be understood that the technology described below is to cover all modifications, equivalents and alternatives falling within the spirit and technical scope of the technology described below.

The terms such as "first," "second," "A," and "B" may be used to describe various constituent elements, but the constituent elements should not be limited by the terms, and these terms are used only to distinguish one constituent element from another constituent element. For example, a first component may be named a second component, and similarly, the second component may also be named the first component, without departing from the scope of the technology described below. The term "and/or" includes any and all combinations of a plurality of the related and listed items. For example, the words 'A and/or B' may be interpreted as 'A or B', 'A', if, and 'both A and B'. In addition, the symbol '/' may be interpreted as 'and' or 'or'.

It should be understood that singular expressions used in the present disclosure include plural expressions unless clearly described as different meanings in the context. In the present disclosure, it should be understood the terms "comprises," "comprising," "includes," "including," "containing," "has," "having" or other variations thereof are inclusive and therefore specify the presence of stated features, numbers, steps, operations, elements, components, or combinations thereof, but do not preclude the presence or addition of one or more other features, numbers, steps, operations, elements, components, or combinations thereof.

When a component, device, element, or the like of the present disclosure is described as having a purpose or performing an operation, function, or the like, the component, device, or element should be considered herein as being "configured to" meet that purpose or to perform that operation or function.

Prior to the detailed description of the drawings, it is intended to clarify that the classification of the configuration portions in this specification is merely classified by a main function that each configuration portion is responsible for. That is, two or more configuration portions to be described below may be combined into one configuration portion, or one configuration portion may be classified into two or more configuration portions according to more subclassified functions. In addition, each of the configuration portions to be described below may additionally perform some or all of the functions of other configuration portions in addition to its own main function, and it goes without saying that some of the main functions of each configuration portion may be performed exclusively by another configuration portion.

In addition, in performing a method or an operation method, each of steps constituting the method may be performed differently from the specified order unless a specific order is clearly stated in the context. That is, each of the steps may be performed in the same order as specified, may be performed substantially simultaneously, or may be performed in the reverse order.

Figure 2:
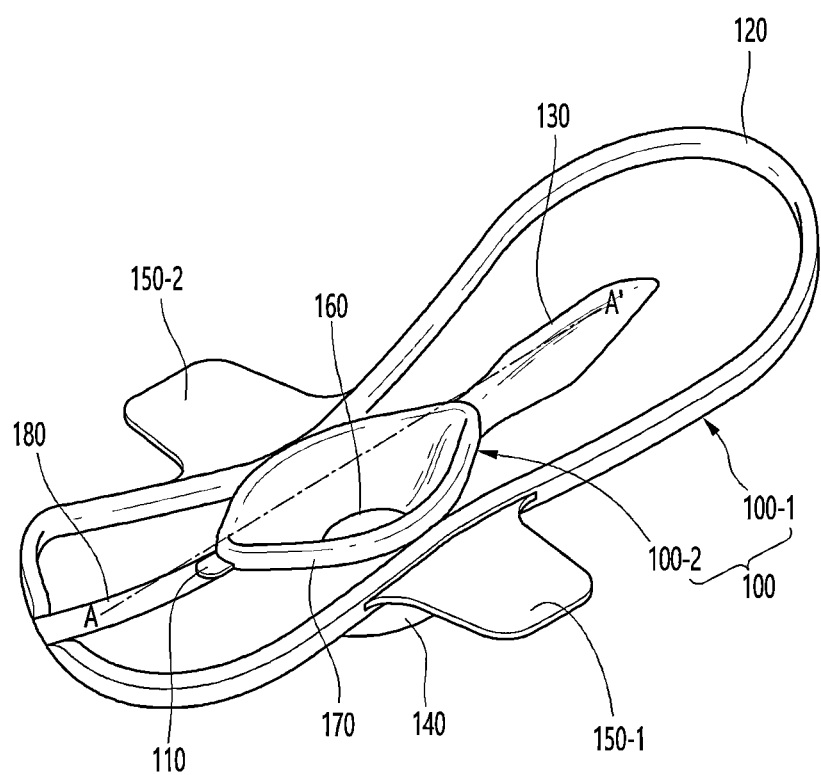
FIG. 2 is a perspective side view of the semipermanent menstrual pad according to the embodiment of the present disclosure.
Figure 3:
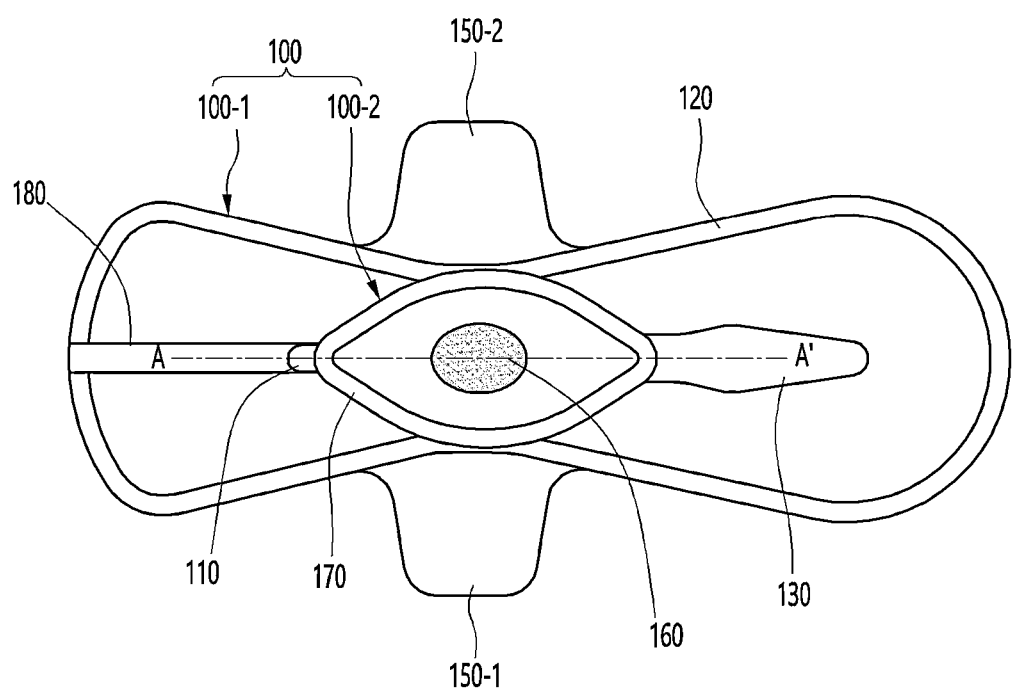
FIG. 3 is a front view of the semipermanent menstrual pad according to the embodiment of the present disclosure.
Figure 4:
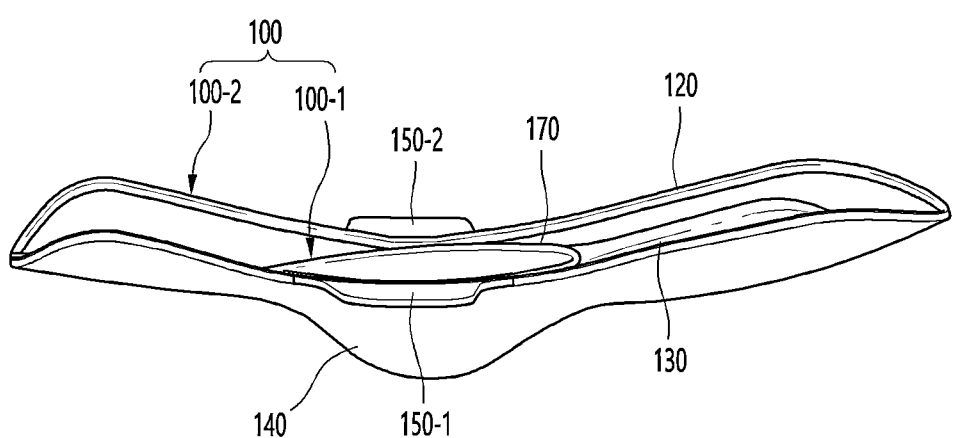
FIG. 4 is a side view of the semipermanent menstrual pad according to the embodiment of the present disclosure.
Figure 5:
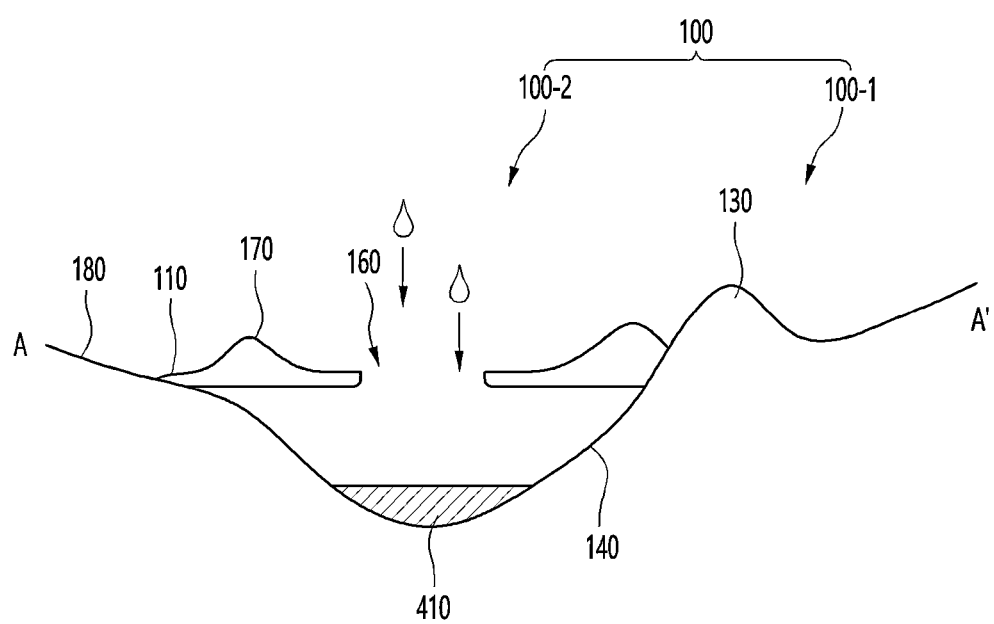
FIG. 5 is an enlarged cross-sectional view of part A-A' of the semipermanent menstrual pad illustrated in FIG. 2.

FIG. 1 is an exploded perspective view of a semipermanent menstrual pad according to an embodiment of the present disclosure, FIG. 2 is a perspective side view of the semipermanent menstrual pad according to the embodiment of the present disclosure, FIG. 3 is a front view of the semipermanent menstrual pad according to the embodiment of the present disclosure, FIG. 4 is a side view of the semipermanent menstrual pad according to the embodiment of the present disclosure, and FIG. 5 is an enlarged cross-sectional view of part A-A' of the semipermanent menstrual pad illustrated in FIG. 2.

Referring to FIGS. 1 to 5, a semipermanent menstrual pad 100 proposed in the present has a structure in which a genital area cover 100-1 is configured as a main body, and a lid part 100-2 is attached to or detached from the genital area cover 100-1. Separate components for performing various functions are provided on the genital area cover 100-1 and the lid part 100-2.

The genital area cover 100-1 may cover a female genital area and have a storage space recessed downward at a center of the genital area cover 100-1 to store menstrual blood. In one embodiment, the genital area cover 100-1 may be made of a soft material that is harmless to the human body and has flexibility. For example, the genital area cover 100-1 may be made of medical silicone or natural rubber. Because the semipermanent menstrual pad 100 is made of medical silicone, there are advantages in that the semipermanent menstrual pad 100 is harmless to the human body, has soft tactility, and causes no inconvenience to the user when the user wears the semipermanent menstrual pad 100. The semipermanent menstrual pad 100 may be disinfected, such that the semipermanent menstrual pad 100 may be semipermanently used.

The genital area cover 100-1 may be divided into a front portion configured to come into direct contact with the female genital area, and a rear portion that is opposite to the front portion and does not come into contact with the genital area cover 100-1. Various constituent elements for storing and treating female user's menstrual blood may be formed/included in the front portion of the genital area cover 100-1.

The lid part 100-2 may cover an upper portion of the storage space 140 to inhibit or prevent the menstrual blood, which is introduced into the storage space formed at the center of the genital area cover 100-1, from leaking to the outside. The lid part 100-2 may be coupled to or separated from the genital area cover 100-1 in an attachable/detachable manner. Like the genital area cover 100-1, the lid part 100-2 may also have a curved shape recessed downward at a center of the lid part 100-2 such that the menstrual blood is guided or introduced to the center thereof and thus the menstrual blood does not easily leak to the outside. The lid part 100-2 may also be made of a soft material that is harmless to the human body and has flexibility. For example, the lid part 100-2 may be made of medical silicone or natural rubber.

The storage space 140 for receiving and storing the introduced menstrual blood may be recessed downward at the central portion of the genital area cover 100-1. The lid part 100-2 may be coupled to and mounted on the genital area cover 100-1 while covering the upper portion of the storage space 140 to prevent the menstrual blood introduced into the storage space 140 from leaking to the outside. Various embodiments related to the coupling/mounting methods may be made. For example, the lid part 100-2 and the genital area cover 100-1 may be coupled to and mounted on each other as a lower region of the lid part 100-2 is fitted with an inlet of the storage space.

In another embodiment, a through-hole 160 may be formed at the center of the lid part 100-2, and the menstrual blood is introduced through the through-hole 160. The menstrual blood having passed through the through-hole 160 is introduced, stored, and contained in the storage space 140. In particular, the storage space 140 and the lid part 100-2 have the central portions having the shapes recessed downward (or formed at positions substantially corresponding to the position of the user's vagina). Therefore, even though the menstrual blood falls onto a periphery of the through-hole 160 without being directly introduced into the through-hole 160, the menstrual blood flows downward along the inclination to the central portion of the semipermanent menstrual pad 100 and then flows into the through-hole 160. Therefore, the menstrual blood may pass through the through-hole 160 and be introduced and stored in the internal/storage space, and the menstrual blood does not leak to the outside.

In one embodiment, to primarily prevent the leak of the menstrual blood, the lid part 100-2 may have a first menstrual blood leak prevention projection 170 formed along a boundary line of the through-hole 160 and provided at a position spaced apart from the through-hole 160 by a preset distance. The first menstrual blood leak prevention projection 170 is provided at a preset height and formed along the boundary line of the through-hole 160 and performs a kind of barrier function for preventing the remaining menstrual blood, which cannot be introduced into the through-hole 160, from leaking to the outside. Therefore, the first menstrual blood leak prevention projection 170 may primarily prevent the leak of the menstrual blood.

The genital area cover 100-1 may have a protruding portion 130 that assists the semipermanent menstrual pad 100 in being appropriately seated and worn on the user's genital area. Various embodiments of the protruding portion 130 may be implemented in consideration of the user's genital area structure. In one form, the protruding portion 130 is seated in a space between the user's buttocks. The protruding portion 130 may extend by a preset length in a first direction from the storage space 140. The protruding portion 130 may also have a height higher than the first menstrual blood leak prevention projection 170 of the lid part 100-2 in the state in which the lid part 100-2 is coupled to the genital area cover 100-1. In this case, as illustrated in FIGS. 1 to 3, the first direction may be a direction toward an end of the genital area cover 100-1. In the state in which the genital area cover 100-1 and the lid part 100-2 are coupled to each other, a distance between the protruding portion 130 and the through-hole 160 of the lid part 100-2 may be set to a distance equal or similar to an average distance from a general female vagina to a space between buttocks. Therefore, the user may wear the semipermanent menstrual pad 100 by seating the protruding portion 130 in the space between the buttocks.

When the user wears the semipermanent menstrual pad 100 while fitting the protruding portion 130 in the space between the buttocks, the semipermanent menstrual pad 100 stably/fixedly covers the genital area without separating from the user's genital area. Therefore, there is no problem with the leak of the menstrual blood caused by the separation of the semipermanent menstrual pad 100. In particular, because a general menstrual pad has a long length in a forward/rearward direction, the separation of the menstrual pad in the forward/rearward direction does not cause a great problem. However, because a length in a transverse direction is comparatively short, the female vagina, from which the menstrual blood is directly secreted, is highly likely to separate from the menstrual pad when the menstrual pad moves in the corresponding direction, which may directly cause the leak of the menstrual blood. However, when the protruding portion 130 is formed, the menstrual pad is fixed by the buttocks positioned at two opposite sides without moving in the transverse direction. Therefore, there is no problem with the leak of the menstrual blood caused by the separation of the menstrual pad 100 in the transverse direction.

The user may separate the lid part 100-2 from the genital area cover 100-1, remove the menstrual blood contained in the storage space 140 to the outside, and clean and reuse the menstrual pad 100. The genital area cover 100-1 may have a discharge guide groove 180 to guide a discharge route for the menstrual blood when the user discharges the menstrual blood to the outside. The discharge guide groove 180 may extend in a second direction from the storage space 140 and connect to the end of the genital area cover 100-1. In this case, the second direction may be a direction opposite to the first direction that is the direction in which the protruding portion 130 extends. To allow the user to easily separate the lid part 100-2 from the genital area cover 100-1, the lid part 100-2 may further include a handle portion 110 extending in the second direction and the upward direction and provided at a position that meets the discharge guide groove 180 in the state in which the lid part 100-2 is coupled to the genital area cover 100-1.

The user may separate the lid part 100-2 from the genital area cover 100-1 and then tilt the semipermanent menstrual pad 100 in the second direction so that the menstrual blood may be discharged to the outside along the discharge guide groove 180 without leaking laterally. As a result, the inside menstrual blood may flow out along the discharge guide groove 180 and be naturally discharged to the outside of the semipermanent menstrual pad 100. Therefore, the user may cleanly remove the menstrual blood without getting the menstrual blood on his/her hands, clean and disinfect the lid part 100-2 and the genital area cover 100-1, couple the lid part 100-2 and the genital area cover 100-1 again, and then reuse the semipermanent menstrual pad 100.

A second menstrual blood leak prevention projection 120 may be formed on a boundary line of the genital area cover 100-1 to secondarily prevent the leak of the menstrual blood together with the first menstrual blood leak prevention projection 170 of the lid part 100-2. Therefore, the first menstrual blood leak prevention projection 170 may primarily prevent the leak of the remaining menstrual blood that cannot be introduced into the storage space 140 through the through-hole 160 of the lid part 100-2. The second menstrual blood leak prevention projection 120 may secondarily prevent the leak of the menstrual blood that leaks while flowing over the first menstrual blood leak prevention projection 170 (i.e., a double menstrual blood leak prevention structure). In particular, because the semipermanent menstrual pad 100 has the structure having the central portion having the shape recessed downward, the menstrual blood very hardly flows over the first and second menstrual blood leak prevention projections 120 and 170 and leaks to the outside of the semipermanent menstrual pad 100. However, the second menstrual blood leak prevention projection 120 is not formed in the discharge guide groove 180 in consideration of the function of the discharge guide groove 180.

In addition, the semipermanent menstrual pad 100 may further include first and second wing portions 150-1 and 150-2 provided at two opposite lateral sides/two opposite sides of the genital area cover 100-1 to prevent the leak of the menstrual blood and perform the function of fixing the semipermanent menstrual pad 100 to the underwear. The first and second wing portions 150-1 and 150-2 may serve to prevent the leak of the menstrual blood that may be caused when the semipermanent menstrual pad 100 separates in the transverse direction. The first and second wing portions 150-1 and 150-2 may respectively have attachment members configured to be attached to or detached from the second and first wing portions 150-2 and 150-1. For example, a button, a Velcro fastener (i.e., a hook-and-loop fastener), or a magnet may be used as the attachment member. Therefore, the user allows the first and second wings 150-1 and 150-2 to be coupled to each other after surrounding the underwear, thereby mounting the semipermanent menstrual pad 100 on the underwear. The user may separate the semipermanent menstrual pad 100 from the underwear by separating the first and second wings 150-1 and 150-2 coupled to each other.

While the drawings have been described separately for convenience of description, it is possible to design a new embodiment by combining the embodiments described in the respective drawings. In addition, the present disclosure is not limited by the configurations and methods of the embodiments as described above, but the embodiments may also be configured by selectively combining a whole or part of the embodiments, such that various modifications can be made.

While the exemplary embodiments have been illustrated and described above, the present specification is not limited to the specific embodiments, and various modifications can of course be made by those having ordinary skill in the art to which the present disclosure pertains without departing from the sprit and scope of the present disclosure. Further, the modifications should not be appreciated individually from the technical spirit or prospect of the present specification.

The present disclosure may be applied to various menstrual pads and various methods of manufacturing menstrual pads.

What is claimed is:

1. A semipermanent menstrual pad comprising:
a genital area cover configured to cover a female genital area and having a storage space recessed at a center of the genital area cover to store menstrual blood; and
a lid part configured to cover an upper portion of the storage space and configured to inhibit the menstrual blood introduced into the storage space from leaking to an outside,
wherein the lid part is configured to be coupled to or separated from the genital area cover,
wherein the lid part comprises:
a through-hole through which the menstrual blood is introduced; and
a first menstrual blood leak prevention projection formed along a boundary line of the through-hole and provided at a position spaced apart from the through-hole by a preset distance and configured to primarily inhibit the leak of the menstrual blood, and
wherein
the storage space configured to be covered by the lid part, and
wherein the genital area cover comprises:
a protruding portion extending from the storage space and protruding in an upward direction so as to be seated in a space between female buttocks; and
a discharge guide groove configured to guide a discharge route for the menstrual blood when the menstrual blood stored in the storage space is discharged to the outside as the lid part is separated from the genital area cover.

2. The semipermanent menstrual pad of claim 1, wherein the genital area cover and the lid part are made of medical silicone.

3. The semipermanent menstrual pad of claim 1, further comprising:
first and second wing portions formed at two opposite sides of the genital area cover and configured to inhibit the leak of the menstrual blood and perform a function of fixing the semipermanent menstrual pad to underwear.

4. The semipermanent menstrual pad of claim 3, wherein the first and second wing portions respectively include attachment members configured to be attached to or detached from the second and first wing portions.

5. The semipermanent menstrual pad of claim 4, wherein the attachment member is a button, a Velcro fastener, or a magnet.

6. The semipermanent menstrual pad of claim 1, wherein a height of the protruding portion is greater than a height of the first menstrual blood leak prevention projection in a state in which the lid part is coupled to the genital area cover.

7. The semipermanent menstrual pad of claim 1, wherein the protruding portion extends in a first direction from the storage space, the discharge guide groove extends in a second direction from the storage space, and the first and second directions are opposite to each other.

8. The semipermanent menstrual pad of claim 7, wherein the discharge guide groove extends in the second direction from the storage space and is formed to an end of the genital area cover.

9. The semipermanent menstrual pad of claim 1, wherein the genital area cover further comprises a second menstrual blood leak prevention projection formed along a boundary line of the genital area cover to secondarily inhibit the leak of the menstrual blood.

10. The semipermanent menstrual pad of claim 9, wherein the second menstrual blood leak prevention projection is not formed in the discharge guide groove.

11. The semipermanent menstrual pad of claim 7, wherein the lid part further includes a handle portion extending in the second direction and the upward direction and provided at a position that meets the discharge guide groove in a state in which the lid part is coupled to the genital area cover so that the lid part is easily separated from the genital area cover.

* * * * *